(12) United States Patent
Griffin, III et al.

(10) Patent No.: US 6,385,489 B1
(45) Date of Patent: May 7, 2002

(54) TRIPLE ARRAY DEFIBRILLATION CATHETER AND METHOD OF USING THE SAME

(75) Inventors: Joseph C. Griffin, III, Atco, NJ (US); Annibale S. Montenero, Rome (IT)

(73) Assignee: EP MedSystems, Inc., West Berlin, NJ (US)

( * ) Notice: Subject to any disclaimer, the term of this patent is extended or adjusted under 35 U.S.C. 154(b) by 0 days.

(21) Appl. No.: 09/399,080

(22) Filed: Sep. 17, 1999

Related U.S. Application Data

(60) Provisional application No. 60/101,865, filed on Sep. 25, 1998.

(51) Int. Cl.[7] .................................................. A61N 5/05
(52) U.S. Cl. .......................................................... 607/5
(58) Field of Search ................................. 607/122, 123, 607/5

(56) References Cited

U.S. PATENT DOCUMENTS 5,545,205 A * 8/1996 Schult et al.
5,697,965 A * 12/1997 Griffin, III
6,122,553 A * 9/2000 Ideker et al.

* cited by examiner

Primary Examiner—Scott M. Getzow
(74) Attorney, Agent, or Firm—Norman E. Lehrer

(57) ABSTRACT

A catheter for facilitating intracardiac atrial defibrillation that includes an elongated flexible member that has a proximal end and a distal end is disclosed. Three spaced apart electrode arrays are secured around the periphery of the flexible member in a predetermined pattern so that a first electrode array is positioned within the superior vena cava, a second electrode array is positioned within the right atrium, and a third electrode array is positioned within the coronary sinus. Alternatively, the third electrode array may be positioned in the right ventricle rather than the coronary sinus. Electrical leads extend through the proximal end of the flexible member to supply electrical current to the electrode arrays, thereby defibrillating or cardioverting the heart.

3 Claims, 2 Drawing Sheets

TRIPLE ARRAY DEFIBRILLATION CATHETER AND METHOD OF USING THE SAME

CROSS REFERENCE TO RELATED APPLICATION

This application claims the benefit of U.S. Provisional Patent Application Ser. No. 60/101,865, filed Sep. 25, 1998.

BACKGROUND OF THE INVENTION

The present invention is directed toward a defibrillation catheter and more particularly, toward a method and apparatus for facilitating intracardiac atrial defibrillation.

Atrial defibrillation is a common arrhythmia that afflicts more than 1.5 million patients in the U.S. alone. It is by far the most prevalent cardiac rhythm disorder associated with hospitalization. Symptoms associated with chronic atrial fibrillation include: awareness of irregularity, palpitations, fatigue, and diminished exercise tolerance. Atrial fibrillation has also been recognized as one of the main contributing factors of embolic strokes.

The risks and symptoms associated with atrial fibrillation confirm the necessity for restoration of sinus rhythm. Two commonly employed methods for performing an intracardiac atrial defibrillation procedure are drug therapy and external cardioversion. With regard to drug therapy, studies have shown that there is a risk for proarrhythmic effects, especially in patients with atrial fibrillation and a history of congestive heart failure, which may outweigh the potential benefit of restoring sinus rhythm.

There are also risks associated with external cardioversion. Such risks result form the fact that high energy shocks (50 to 360 Joules) are used during the procedure. The high energy shocks can cause heavy muscular contractions with a potential risk of spine or bone fractures, potential pronounced increase in muscle enzymes, induction of ventricular arrhythmias, and overall negative influence on myocardial function. Further, the high energy shocks require the administration of a general anesthetic.

In recognition of the foregoing, a method involving internal cardioversion using percutaneous transvenous catheter electrodes has been developed. Internal cardioversion can be performed with energies of less than 12 Joules. However, existing multi-electrode catheters typically do not have the proper arrangement of electrodes to provide the necessary electroshocks to the appropriate locations.

SUMMARY OF THE INVENTION

The present invention is designed to overcome the deficiencies of the prior art discussed above. It is an object of the present invention to provide a catheter for facilitating atrial defibrillation that uses three electrode arrays on a single catheter.

It is a further object of the present invention to provide a method of performing intracardiac atrial defibrillation.

In accordance with the illustrative embodiments demonstrating features and advantages of the present invention, there is provided a catheter for facilitating intracardiac atrial defibrillation that includes an elongated flexible member that has a proximal end and a distal end. Three spaced apart electrode arrays are secured around the periphery of the flexible member in a predetermined pattern so that a first electrode array is adapted to positioned within the superior vena cava, a second electrode array is adapted to be positioned within the right atrium, and a third electrode array is adapted to be positioned within the coronary sinus. Alternatively, the third electrode array may be positioned in the right ventricle rather than the coronary sinus. Electrical leads extend through the flexible member to supply electrical current to the electrode arrays.

Other objects, features, and advantages of the invention will be readily apparent from the following detailed description of preferred embodiments thereof taken in conjunction with the drawings.

BRIEF DESCRIPTION OF THE DRAWINGS

For the purpose of illustrating the invention, there is shown in the accompanying drawings forms which are presently preferred, it being understood that the invention is not intended to be limited to the precise arrangements and instrumentalities shown.

DETAILED DESCRIPTION OF THE PREFERRED EMBODIMENT

Figure 1:
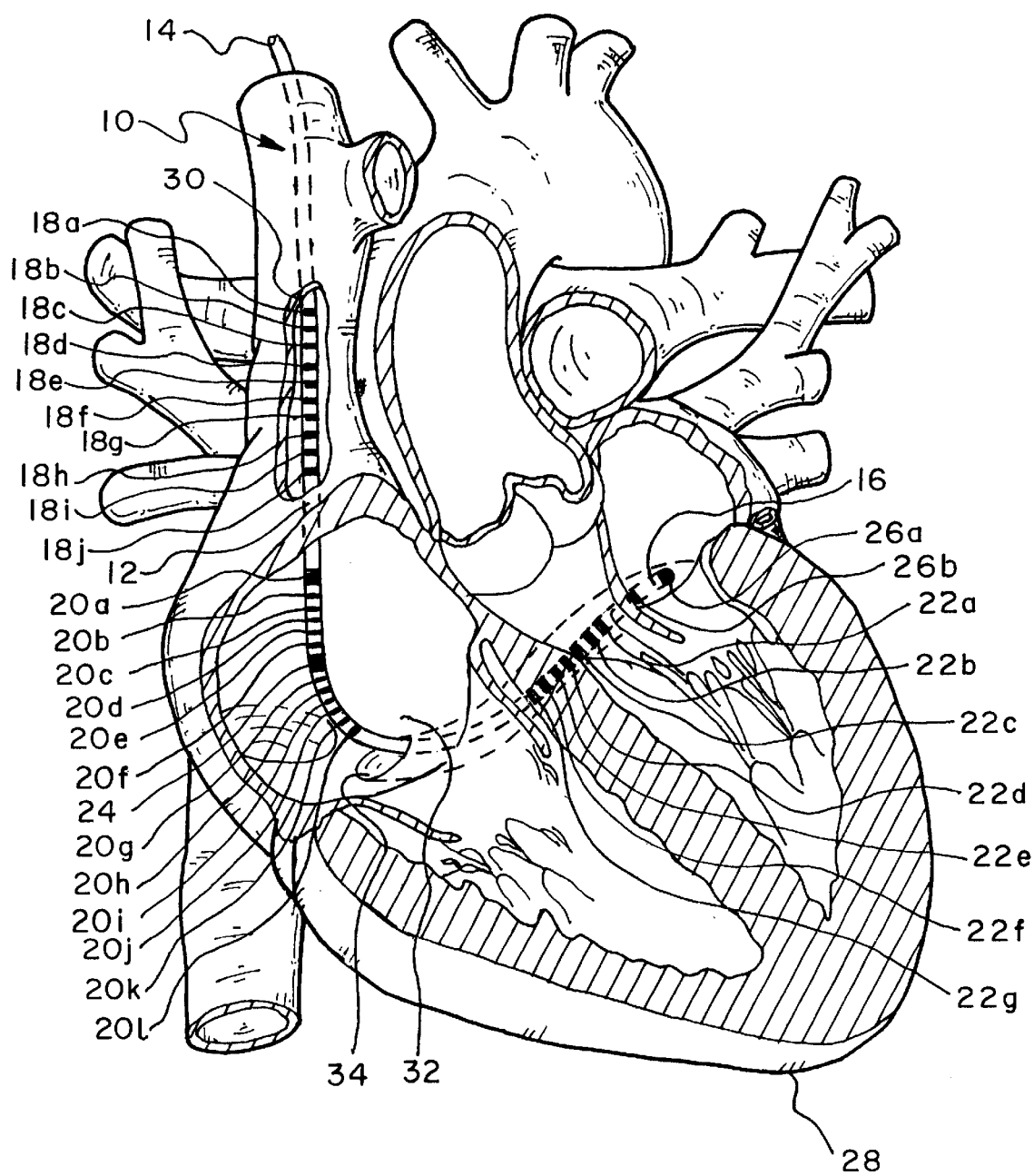
FIG. 1 is a partial plan view of the first embodiment of the catheter of the present invention inserted into a heart and FIG. 2 is a partial plan view of the second embodiment of the catheter of the present invention inserted into a heart.

Referring now to the drawings in detail wherein like reference numerals have been used throughout the various figures to designate like elements, there is shown in FIG. 1 a catheter constructed in accordance with the principles of the present invention and designated generally as 10.

In a first embodiment of the present invention, as seen in FIG. 1, the catheter 10 essentially includes an elongated flexible member 12 which may be made of polyurethane. However, the flexible member 12 may be made from a variety of materials such as silicone rubber or plasticized PVC. The flexible member 12 is preferably approximately 110 centimeters long with an outside diameter of approximately 2.5 millimeters. As should be readily apparent to those skilled in the art, only the working portion of the catheter 10 is shown in the drawings.

The working portion of the flexible member 12 has a proximal end 14 and a distal end 16. Carried on the working portion of the flexible member 12 of the catheter 10 are first, second, and third spaced apart electrode arrays, the details of which will be described hereinafter. Electrical wires (not shown) from the electrode arrays pass through the interior of the flexible member 12 to a manifold secured to the remote end of the flexible member 12 for connecting the catheter 10 to appropriate electronic equipment.

Located adjacent the proximal end 14 is the first electrode array. The array includes approximately ten electrodes 18a–18j where each electrode has an approximate length of five millimeters and each electrode is spaced approximately five millimeters away from each adjacent electrode. The second electrode array, located distal to the first array, consists of approximately twelve electrodes 20a–20l. The length of each of these electrodes is also approximately five millimeters and each electrode is spaced approximately five millimeters away from each adjacent electrode. The third electrode array, located adjacent the distal end 16 consists of approximately seven electrodes 22a–22g. The length of each of these electrode is approximately five millimeters and each is spaced approximately ten millimeters away from each adjacent electrode.

Located within the second array of electrodes 20a–20l is an atrial pacing/sensing electrode 24. Also, located at the distal end 16 of the flexible member 12 are bi-polar pacing/ sensing stimulation electrodes 26a and 26b. A steering arrangement known in the art may be associated with the catheter 10 in order to direct the placement of the electrode arrays.

In order to perform a defibrillation procedure, the flexible member 12 is introduced into the vascular system from the jugular area in a manner known in the art. The flexible member 12 is then guided into the patient's heart 28 until it is placed in the desired position. The flexible member 12 is positioned so that the first electrode array 18a–18j is positioned within the superior vena cava 30, the second electrode array 20a–20l is positioned within the right atrium 32, and the distal end 16 with the third electrode array 22a–22g is positioned within the coronary sinus 34.

With the flexible member 12 properly in place, electric shocks are applied through the catheter in order to defibrillate the patient's heart 28. This is accomplished by connecting the contact pin (not shown) at the proximal end of the proximal lead (not shown) attached to the first and second electrode arrays and the contact pin (not shown) of the distal lead of the third electrode array to an appropriate power source. Thereafter, low energy electrical current is supplied through the electrical leads to the corresponding electrode arrays in order to achieve a normal sinus rhythm in the patient.

More specifically, the atrial pacing/sensing electrode 24 and the bi-polar pacing/sensing stimulation electrodes 26a and 26b, sense the occurrence, if any, of fibrillation. If fibrillation is sensed, the heart 28 is defibrillated or cardioverted by the application of at least one electrical shock between the first and second arrays of electrodes 18a–18j and 20a–20l, respectively, which are connected to the proximal electrical lead and the third array of electrodes 22a–22g which is connected to the distal electrical lead. The two proximal common arrays 18a–18j and 20a–20l on the catheter are coupled together as an anode and the single array 22a–22g on the distal end 16 of the catheter is a cathode. The polarity of the arrays can be reversed to attempt lower defibrillation thresholds in certain patients. Approximately 1–50 Joules of energy are discharged through the sinoatrial node and the atrioventricular node to terminate atrial fibrillation.

Figure 2:
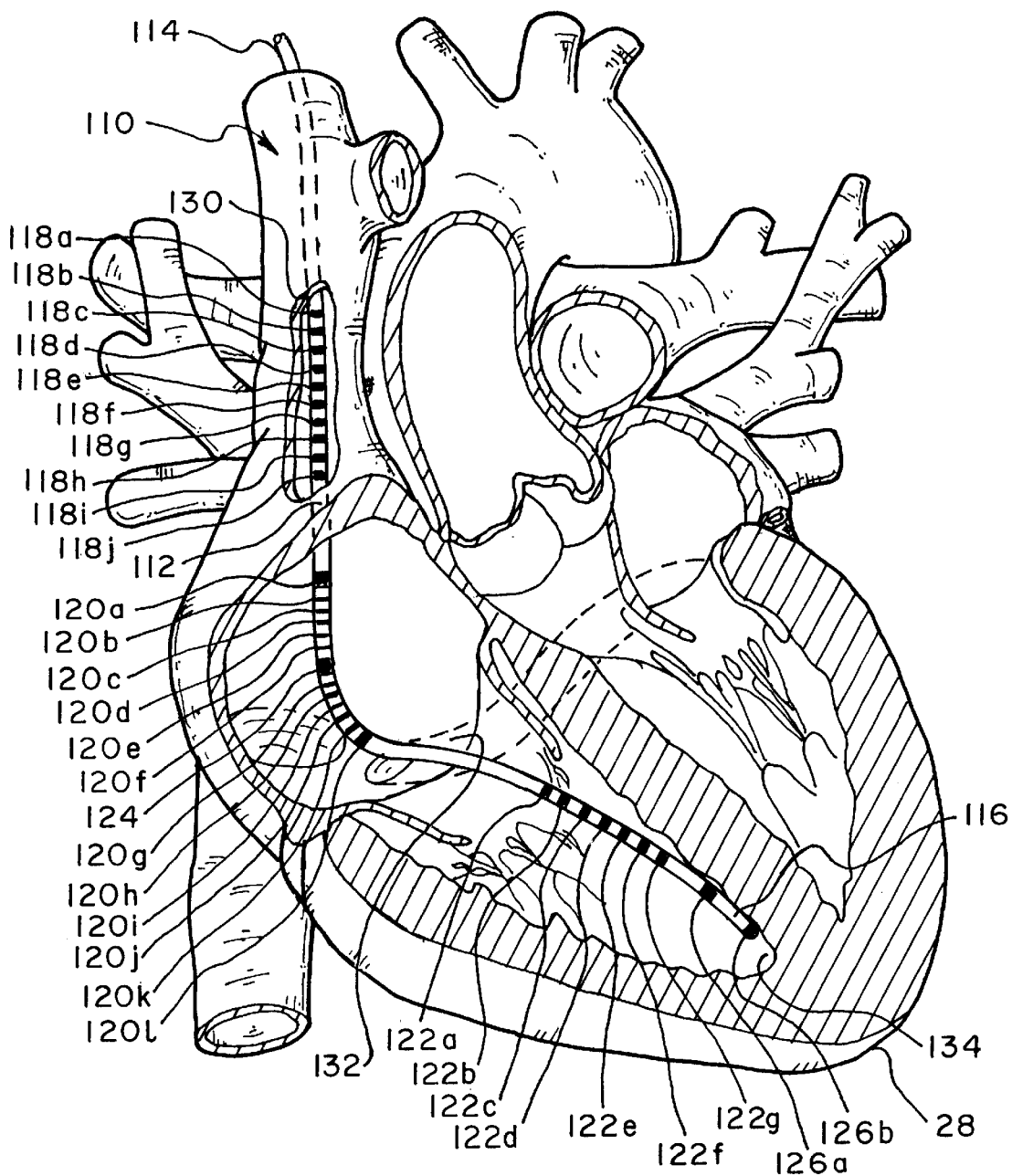

In a second embodiment of the present invention, as seen in FIG. 2, the catheter 110, similar to the catheter of the first embodiment, includes an elongated flexible member 112 which may be made of the same types of materials and have the same dimensions as discussed above. Again, only the working portion of the catheter 110 is shown.

The working portion of the flexible member 112 has a proximal end 114 and a distal end 116. Carried on the working portion of the flexible member 112 of the catheter 110 are first, second; and third spaced apart electrode arrays, the details of which will be described hereinafter. Electrical wires (not shown) from the electrode arrays pass through the interior of the flexible member 112 to a manifold secured to the remote end of the flexible member 112 for connecting the catheter 110 to appropriate electronic equipment.

Located adjacent the proximal end 114 is the first electrode array. The array includes approximately ten electrodes 118a–118j where each electrode has an approximate length of five millimeters and each electrode is spaced approximately five millimeters away from each adjacent electrode. The second electrode array, located distal to the first array, consists of approximately twelve electrodes 120a–120l. The length of each of these electrodes is also approximately five millimeters and each electrode is spaced approximately five millimeters away from each adjacent electrode. The third electrode, located adjacent the distal end 116 consists of approximately seven electrodes 122a–122g. The length of each of these electrode is approximately five millimeters and each is spaced approximately ten millimeters away from each adjacent electrode.

Located within the second array of electrodes 120a–120l is an atrial pacing/sensing electrode 124. Also, located at the distal end 116 of the flexible member 112 are bi-polar pacing/sensing stimulation electrodes 126a and 126b. A steering arrangement known in the art may be associated known with the catheter 110 in order to direct the placement of the electrode arrays.

In order to perform a defibrillation procedure, the flexible member 112 is introduced into the vascular system from the jugular area in a manner known in the art. The flexible member 112 is then guided into the patient's heart 128 until it is placed in the desired position. The flexible member 112 is positioned so that the first electrode array 118a–118j is positioned within the superior vena cava 130, the second electrode array 120a–120l is positioned within the right atrium 132, and the distal end 116 with the third electrode array 122a–122g is positioned within the right ventricle 134 instead of the coronary sinus, as in the first embodiment, in an attempt to obtain lower defibrillation thresholds.

With the flexible member 112 properly in place, electric shocks are applied through the catheter in order to defibrillate the patient's heart. This is accomplished by connecting the contact pin (not shown) at the proximal end of the proximal lead (not shown) attached to the first and second electrode arrays 118a–118j and 120a–120l, respectively, and the contact pin (not shown) of the distal lead of the third electrode array 122a–122g to an appropriate power source. Thereafter, low energy electrical current is supplied through the electrical leads to the corresponding electrode arrays in order to achieve a normal sinus rhythm in the patient.

More specifically, the atrial pacing/sensing electrode 124 and the bi-polar pacing/sensing stimulation electrodes 126a and 126b, sense the occurrence, if any, of fibrillation. If fibrillation is sensed, the heart 128 is defibrillated or cardioverted by the application of at least one electrical shock between the first and second arrays of electrodes 118a–118j and 120a–120l, respectively, which are connected to the proximal electrical lead and the third array of electrodes 122a–122g which is connected to the distal electrical lead. The two proximal common arrays 118a–118j and 120a–120l on the catheter are coupled together as an anode and the single array 122a–122g on the distal end 116 of the flexible member 112 is a cathode. The polarity of the arrays can be reversed to attempt lower defibrillation thresholds in certain patients. As in the first embodiment, approximately 1–50 Joules of energy are discharged through the sinoatrial node and the atrioventricular node to terminate atrial fibrillation.

It should be noted that in both of the embodiments, a continuous flexible electrode may be substituted for any or all of the electrode arrays. This ensures that the electrode is sufficiently flexible so that the same can be easily bent and straightened, as desired, without causing damage to the same. Such an electrode is preferably formed by a process of ion-beam assisted deposition (IBAD). This technology is described in detail in each of U.S. Pat. Nos. 5,468,562; 5,474,797; and 5,492,763, the disclosures of which are incorporated herein by reference. The use of this technique for forming an electrode catheter is also described in co-pending application Ser. No. 08/751,436, filed on Nov. 20, 1996, entitled "Temporary Atrial Defibrillation Catheter with Improved Electrode Configuration and Method of Fabrication." The subject matter of this co-pending application, commonly owned, is also incorporated herein by reference. The electrodes may also be applied by sputtering, vacuum deposition, printing, or spraying.

An advantage of the present system is that it is easy to use because only one catheter is needed. That is, the three electrode arrays are combined onto one single catheter. It is far easier and faster for physicians to place one catheter, as opposed to two separate devices, in a patient. Also, it is less traumatic and safer for the patient to have one catheter placed within his or her body as opposed to two or more devices.

Another advantage of the present system is that it is easier to use than pulmonary artery defibrillation catheters because electrophysiologists are more familiar with superior vena cava, right atrium, and coronary sinus catheter placement which is routinely used in their practice as opposed to pulmonary artery placement which is used more in pressure monitoring in critical care.

The present invention may be embodied in other forms without departing from the spirit or essential attributes thereof and accordingly, reference should be made to the claims rather than to the foregoing specification as indicating the scope thereof.

We claim:

1. A method for facilitating intracardiac atrial defibrillation in a patient comprising the steps of:

providing a unitary elongated flexible member with a proximal end and a distal end and first, second, and third spaced apart electrode arrays secured around the periphery of said flexible member wherein said electrode arrays are arranged in a predetermined pattern;

positioning said elongated flexible member within the patient's heart;

positioning said first electrode array within the superior vena cava, positioning said second electrode array within the right atrium, and positioning said third electrode array within the coronary sinus; and applying electric shocks through said elongated flexible member in order to defibrillate the patient's heart.

2. The method for facilitating intracardiac atrial defibrillation in a patient as claimed in claim 1 wherein the step of positioning the electrode arrays includes positioning said first electrode array within the superior vena cava, positioning said second electrode array within the right atrium, and positioning said third electrode array within the right ventricle.

3. The method for facilitating intracardiac atrial defibrillation in a patient as claimed in claim 1 further including an atrial pacing/sensing electrode and bi-polar pacing/sensing stimulation electrodes located on said flexible member and which sense the occurrence of fibrillation.

* * * * *